(12) United States Patent
Hashimoto

(10) Patent No.: US 6,464,644 B2
(45) Date of Patent: Oct. 15, 2002

(54) METHOD OF ULTRASONIC IMAGING AND ULTRASONIC DIAGNOSTIC APPARATUS

(75) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 2 days.

(21) Appl. No.: 09/777,984

(22) Filed: Feb. 6, 2001

(65) Prior Publication Data

US 2001/0021810 A1 Sep. 13, 2001

(30) Foreign Application Priority Data

Mar. 8, 2000 (JP) ........................................ 2000-063853

(51) Int. Cl.$^7$ ................................................. A61B 8/00
(52) U.S. Cl. ..................................................... 600/458
(58) Field of Search ................................ 600/437, 439, 600/443, 447, 454–456, 458

(56) References Cited

U.S. PATENT DOCUMENTS

| | | |
|---|---|---|
| 5,694,937 A | 12/1997 | Kamiyama |
| 5,735,281 A | 4/1998 | Rafter et al. |
| 5,944,666 A | 8/1999 | Hossack et al. |
| 5,947,904 A * | 9/1999 | Hossack et al. ............ 600/458 |
| 5,971,928 A * | 10/1999 | Dodd et al. ................. 600/458 |
| 6,245,019 B1 * | 6/2001 | Kamiyama ................... 600/458 |

FOREIGN PATENT DOCUMENTS

| | | |
|---|---|---|
| DE | 19723053 | 2/1998 |
| WO | 9908599 | 2/1999 |

* cited by examiner

*Primary Examiner*—Francis J. Jaworski
(74) *Attorney, Agent, or Firm*—Moonray Kojima

(57) ABSTRACT

An ultrasonic diagnostic apparatus transmits ultrasonic waves at such a strength as to disperse the contrast agent for part of a number of sonic beams which form one frame and at such a strength as not to disperse the contrast agent for other sonic beams thereby to produce an image for a marking frame from received echo signals of ultrasonic transmission, and subsequently transmits ultrasonic waves successively at such a strength as not to disperse the contrast agent for all sonic beams thereby to produce images continuously for no-marking frames, and, after such a time length that the flow range is present within the view field, produces an image for another marking frame. These operations are repeated to display ultrasonic images by which it is possible to visually recognize at a glance the time-wise change of a blood flow.

14 Claims, 6 Drawing Sheets

Marking frame

No- marking frame

First marking frame

No-marking frame

Second marking frame

Marking frame

No- Marking frame

Marking frame

No- Marking frame

Marking frame

Marking frame

No- Marking frame

METHOD OF ULTRASONIC IMAGING AND ULTRASONIC DIAGNOSTIC APPARATUS

BACKGROUND OF THE INVENTION

The present invention relates to a method of ultrasonic imaging and an ultrasonic diagnostic apparatus, and more particularly to a method of ultrasonic imaging and an ultrasonic diagnostic apparatus capable of producing ultrasonic images by which it is possible to visually recognize at a glance the time-wise change of a blood flow.

In obtaining an ultrasonic image of a blood flow, there has been a convention to use small bubbles in blood as the contrast agent. These small bubbles disperse by being hit by a strong ultrasonic wave.

On this account, after the imaging for a high-transmission frame (a frame taken by use of an ultrasonic wave which is strong enough to disperse the contrast agent), imaging for low-transmission frames (frames taken by use of an ultrasonic wave which is not so strong as to disperse the contrast agent) is carried out continuously, and imaging for another high-transmission frame is carried out on expiration of the time at which the view field is filled with a blood flow including the contrast agent, with these operations being implemented cyclically, as shown in FIG. 1.

In FIG. 1, vertical line segments aligning along the time axis represent transmission time points and transmission strengths of sonic beams which form the frames.

FIG. 2(a) shows sonic beams which form a high-transmission frame, and the bold lines signify an ultrasonic wave which is strong enough to disperse the contrast agent. Indicated by V is a blood vessel, and the arrow indicates the direction of blood flow.

In contrast, FIG. 2(b) shows sonic beams which form a low-transmission frame, and the thin lines signify an ultrasonic wave which is not so strong as to disperse the contrast agent.

It has been possible to view the state of a blood flow at one moment in the image of a high-transmission frame which is taken based on the above-mentioned conventional scheme.

However, this scheme has been problematic in that it cannot provide a view of the time-wise change of a blood flow. Specifically, if it is intended to view the time-wise change of a blood flow, it is necessary to compare images of high-transmission frames taken at different time points, and it necessitates skill.

SUMMARY OF THE INVENTION

It is an object of the present invention to provide a method of ultrasonic imaging and an ultrasonic diagnostic apparatus capable of producing ultrasonic images by which it is possible to visually recognize at a glance the time-wise change of a blood flow.

At a first viewpoint, the present invention provides a method of ultrasonic imaging which is characterized by transmitting an ultrasonic wave at such a strength as to disperse the contrast agent for part of a number of sonic beams which form one frame and transmitting an ultrasonic wave at such a strength as not to disperse the contrast agent for other sonic beams, and producing an image for one frame from received signals which correspond to the ultrasonic wave transmission.

In the ultrasonic imaging method of the first viewpoint, the contrast agent in one part of the image disperses, while the contrast agent in other part does not disperse. Therefore, when another imaging takes place after such a time length that the flow range is present within the view field, the portion with the contrast agent being dispersed moves slightly in its position on the image. When this operation is repeated for a flow which intersects the direction of sonic beam, an effect similar to the tagging in magnetic resonance imaging emerges, and the flow seems to have a stripe pattern indicative of the passing time. As a result, it becomes possible to visually recognize the time-wise change of a blood flow at a glance.

At a second viewpoint, the present invention provides a method of ultrasonic imaging which is characterized by transmitting an ultrasonic wave at such a strength as not to disperse the contrast agent for all of a number of sonic beams which form one frame, producing an image for one frame from received signals which correspond to the ultrasonic wave transmission, and interposing the formed frame between frames which are produced by the ultrasonic imaging method mentioned in the first viewpoint.

In the ultrasonic imaging method of the second viewpoint, a frame without the dispersion of contrast agent is interposed between frames with the dispersion of contrast agent in part of the image, whereby the real-time property of progressive imaging can be improved.

At a third viewpoint, the present invention provides a method of ultrasonic imaging which is derived from the method of the second viewpoint, and is characterized in that one timing of ultrasonic wave transmission for one frame at such a strength as to disperse the contrast agent and another timing of ultrasonic wave transmission for a later frame at such a strength as to disperse the contrast agent have a time difference which is based on the heart beat.

In the ultrasonic imaging method of the third viewpoint, there is provided a time difference between events of transmission by which the contrast agent is dispersed in part of the image, whereby a pulsing flow can be observed properly.

At a fourth viewpoint, the present invention provides a method of ultrasonic imaging which is derived from the method of the third viewpoint, and is characterized in that there are in one frame at least two spaced-out sonic beams for which an ultrasonic wave is transmitted at such a strength as to disperse the contrast agent.

In the ultrasonic imaging method of the fourth viewpoint, the contrast agent disperses at least two spaced-out positions, whereby a number of stripe patterns can be appended to a flow at the same time.

At a fifth viewpoint, the present invention provides a method of ultrasonic imaging which is characterized by transmitting an ultrasonic wave at such a strength as to disperse the contrast agent for a certain depth of a number of sonic beams which form one frame or a certain depth seen from the ultrasonic probe and transmitting an ultrasonic wave at such a strength as not to disperse the contrast agent for other depths, and producing an image for one frame from received signals which correspond to the ultrasonic wave transmission.

In the ultrasonic imaging method of the fifth viewpoint, the contrast agent in one part of the image disperses, whereas the contrast agent in other part does not disperse. Therefore, when another imaging takes place after such a time length that the flow range is present within the view field, the portion with the contrast agent being dispersed moves slightly in its position on the image. When this operation is repeated for a flow which intersects the direction of sonic beam, an effect similar to the tagging in magnetic resonance imaging emerges, and the flow seems to have a stripe pattern indicative of the passing time. Whereby, it becomes possible to visually recognize at a glance the time-wise change of a blood flow.

At a sixth viewpoint, the present invention provides a method of ultrasonic imaging which is characterized by transmitting an ultrasonic wave at such a strength as not to disperse the contrast agent for all of a number of sonic beams which form one frame, producing an image for one frame from received signals which correspond to the ultrasonic wave transmission, and interposing the formed frame between frames which are produced by the ultrasonic imaging method mentioned in the fifth viewpoint.

In the ultrasonic imaging method of the sixth viewpoint, a frame without the dispersion of contrast agent is interposed between frames with the dispersion of contrast agent in part of the image, whereby the real-time property of progressive imaging can be improved.

At a seventh viewpoint, the present invention provides a method of ultrasonic imaging which is derived from the method of the sixth viewpoint, and is characterized in that one timing of ultrasonic wave transmission for one frame at such a strength as to disperse the contrast agent and another timing of ultrasonic wave transmission for a later frame at such a strength as to disperse the contrast agent have a time difference which is based on the heart beat.

In the ultrasonic imaging method of the seventh viewpoint, there is provided a time difference between events of transmission by which the contrast agent is dispersed in part of the image, whereby a pulsing flow can be observed properly.

At an eighth viewpoint, the present invention provides a method of ultrasonic imaging which is derived from the method of the seventh viewpoint, and is characterized in that there are in one frame at least two spaced-out positions of depths for which an ultrasonic wave is transmitted at such a strength as to disperse the contrast agent.

In the ultrasonic imaging method of the eighth viewpoint, the contrast agent disperses at least two spaced-out positions, whereby a number of stripe patterns can be appended to the flow at the same time.

At a ninth viewpoint, the present invention provides a method of ultrasonic imaging characterized by combining an ultrasonic imaging method of the first through fourth viewpoints and an ultrasonic imaging method of the fifth through eighth viewpoints.

In the ultrasonic imaging method of the ninth viewpoint, stripe patterns are appended to both of a flow which intersects the direction of sonic beam and a flow which is virtually parallel to the direction of sonic beam, whereby it is particularly suitable to observe a two-dimensional flow of the cardiac ventricle and atrium.

At a tenth viewpoint, the present invention provides an ultrasonic diagnostic apparatus characterized by comprising an ultrasonic probe, a transmission/reception means which transmits an ultrasonic wave from the ultrasonic probe and receives a signal which corresponds to the ultrasonic wave transmission, a transmission strength control means which controls the ultrasonic wave transmission to have such a strength as to disperse the contrast agent for part of a number of sonic beams which form one frame and have such a strength as not to disperse the contrast agent for other sonic beams, and an image producing means which produces an image for one frame from the received signals.

The ultrasonic diagnostic apparatus of the tenth viewpoint can suitably carry out the ultrasonic imaging method of the first viewpoint.

At an eleventh viewpoint, the present invention provides an ultrasonic diagnostic apparatus which is derived from the apparatus of the tenth viewpoint and is characterized in that the transmission strength control means controls the ultrasonic wave transmission such that one frame, which is formed at such a strength as not to disperse the contrast agent for all of a number of sonic beams which form one frame, is interposed between frames which are formed by the ultrasonic wave transmission at such a strength as to disperse the contrast agent for part of a number of sonic beams which form one frame and the ultrasonic wave transmission at such a strength as not to disperse the contrast agent for other sonic beams.

The ultrasonic diagnostic apparatus of the eleventh viewpoint can suitably carry out the ultrasonic imaging method of the second viewpoint.

At an twelfth viewpoint, the present invention provides an ultrasonic diagnostic apparatus which is derived from the apparatus of the eleventh viewpoint and is characterized in that the transmission strength control means controls the ultrasonic wave transmission such that one timing of ultrasonic wave transmission for one frame at such a strength as to disperse the contrast agent and another timing of ultrasonic wave transmission for a later frame at such a strength as to disperse the contrast agent have a time difference which is based on the heart beat.

The ultrasonic diagnostic apparatus of the twelfth viewpoint can suitably carry out the ultrasonic imaging method of the third viewpoint.

At a thirteenth viewpoint, the present invention provides an ultrasonic diagnostic apparatus which is derived from an apparatus of the tenth through twelfth viewpoints and is characterized in that the transmission strength control means controls the ultrasonic wave transmission such that there are in one frame at least two spaced-out sonic beams for which an ultrasonic wave is transmitted at such a strength as to disperse the contrast agent.

The ultrasonic diagnostic apparatus of the thirteenth viewpoint can suitably carry out the ultrasonic imaging method of the fourth viewpoint.

At a fourteenth viewpoint, the present invention provides an ultrasonic diagnostic apparatus characterized by comprising an ultrasonic probe, a transmission/reception means which transmits an ultrasonic wave from the ultrasonic probe and receives a signal which corresponds to the ultrasonic wave transmission, a transmission strength control means which controls the ultrasonic wave transmission to have such a strength as to disperse the contrast agent for a certain depth of a number of sonic beams which form one frame or a certain depth seen from the ultrasonic probe and have such a strength as not to disperse the contrast agent for other depths, and an image producing means which produces an image for one frame from the received signals.

The ultrasonic diagnostic apparatus of the fourteenth viewpoint can suitably carry out the ultrasonic imaging method of the fifth viewpoint.

At a fifteenth viewpoint, the present invention provides an ultrasonic diagnostic apparatus which is derived from the apparatus of the fourteenth viewpoint and is characterized in that the transmission strength control means controls the ultrasonic wave transmission such that one frame, which is formed by the ultrasonic wave transmission at such a strength as not to disperse the contrast agent for all of a number of sonic beams which form one frame, is interposed between frames which are formed by the ultrasonic wave transmission at such a strength as to disperse the contrast agent for a certain depth of a number of sonic beams which form one frame or a certain depth seen from the ultrasonic probe and at such a strength as not to disperse the contrast agent for other depths.

The ultrasonic diagnostic apparatus of the fifteenth viewpoint can suitably carry out the ultrasonic imaging method of the sixth viewpoint.

At a sixteenth viewpoint, the present invention provides an ultrasonic diagnostic apparatus which is derived from the apparatus of the fifteenth viewpoint and is characterized in that the transmission strength control means controls the ultrasonic wave transmission such that one timing of ultrasonic wave transmission for one frame at such a strength as to disperse the contrast agent and another timing of ultrasonic wave transmission for a later frame at such a strength as to disperse the contrast agent have a time difference which is based on the heart beat.

The ultrasonic diagnostic apparatus of the sixteenth viewpoint can suitably carry out the ultrasonic imaging method of the seventh viewpoint.

At a seventeenth viewpoint, the present invention provides an ultrasonic diagnostic apparatus which is derived from an apparatus of the fourteenth through sixteenth viewpoints and is characterized in that the transmission strength control means controls the ultrasonic wave transmission such that there are in one frame at least two spaced-out positions of depths for which an ultrasonic wave is transmitted at such a strength as to disperse the contrast agent.

The ultrasonic diagnostic apparatus of the seventeenth viewpoint can suitably carry out the ultrasonic imaging method of the eighth viewpoint.

At an eighteenth viewpoint, the present invention provides an ultrasonic diagnostic apparatus characterized by comprising an ultrasonic probe, a transmission/reception means which transmits an ultrasonic wave from the ultrasonic probe and receives a signal which corresponds to the ultrasonic wave transmission, a transmission strength control means which controls the ultrasonic wave transmission to have such a strength as to disperse the contrast agent for part of a number of sonic beams which form one frame and have for other sonic beams such a strength as to disperse the contrast agent for a certain depth of the sonic beams or a certain depth seen from the ultrasonic probe and have such a strength as not to disperse the contrast agent for other depths, and an image producing means which produces an image for one frame from the received signals.

The ultrasonic diagnostic apparatus of the eighteenth viewpoint can suitably carry out the ultrasonic imaging method of the ninth viewpoint.

According to the ultrasonic imaging method and ultrasonic diagnostic apparatus of this invention, which actively utilize the dispersion of contrast agent in the presence of a strong ultrasonic wave, it is possible to produce ultrasonic images which enable to visually recognize at a glance the time-wise change of a blood flow.

Further objects and advantages of the present invention will be apparent from the following description of the preferred embodiments of the invention as illustrated in the accompanying drawings.

DETAILED DESCRIPTION OF THE INVENTION

The present invention will be explained in more detail by dealing with the illustrated embodiments.

Figure 1:
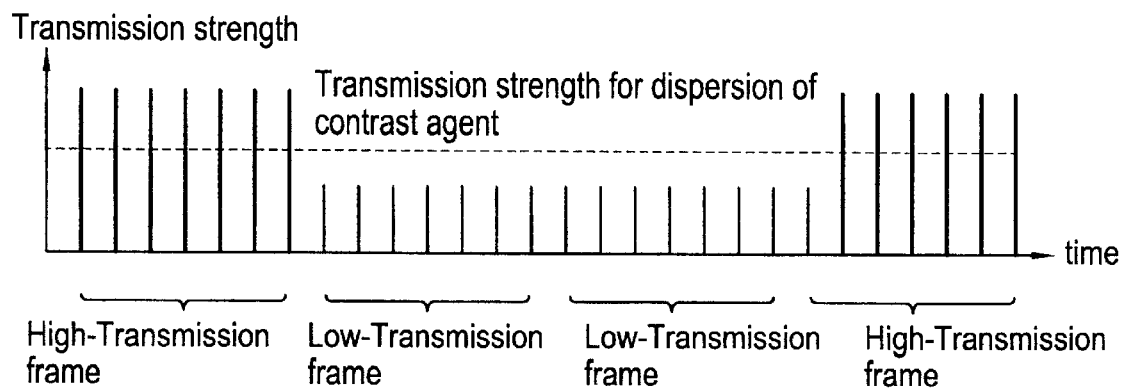
FIG. 1 is an explanatory diagram showing the transmission order for forming high-transmission frames and low-transmission frames based on the conventional scheme.
Figure 2A:
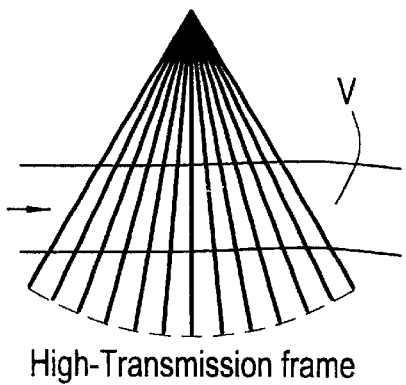
FIG. 2 is an explanatory diagram of the high-transmission frame and low-transmission frame based on the conventional scheme.
Figure 2B:
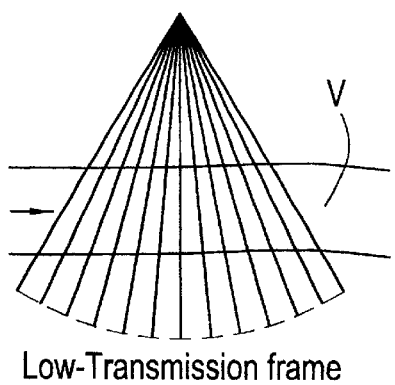
Figure 3:
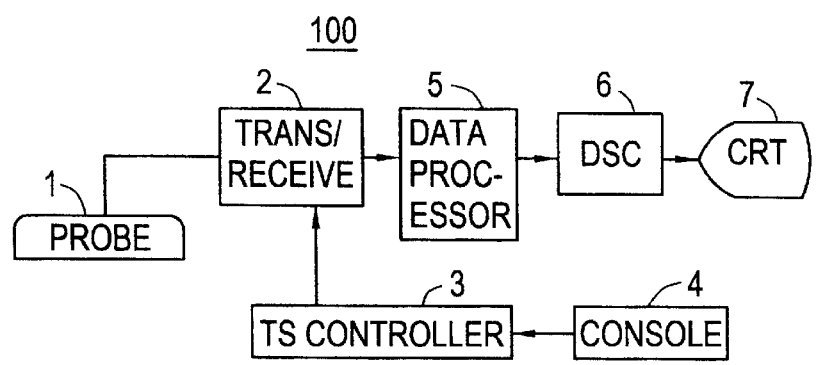
FIG. 3 is a block diagram of an ultrasonic diagnostic apparatus based on the first embodiment.

First embodiment:

FIG. 3 is a block diagram of an ultrasonic diagnostic apparatus 100 based on the first embodiment of this invention.

This ultrasonic diagnostic apparatus 100 is made up of an ultrasonic probe 1, a transmitter/receiver 2 which transmits an ultrasonic wave at a specified transmission strength, receives the echo of ultrasonic transmission, and produces a reception signal, a transmission strength controller 3 which specifies the transmission strength, an operation console 4 which is used by the operator to instruct the transmission strength controller 3, a data processor 5 which produces an ultrasonic image such as a B-mode image from the reception signal, a DSC (digital scan converter) 6 which converts the ultrasonic image into a display image, and a CRT 7 which displays the display image.

Figure 4A:
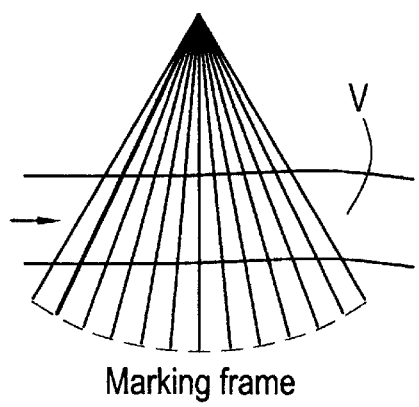
FIG. 4 is an explanatory diagram of a marking frame and no-marking frame based on the first embodiment.
Figure 4B:
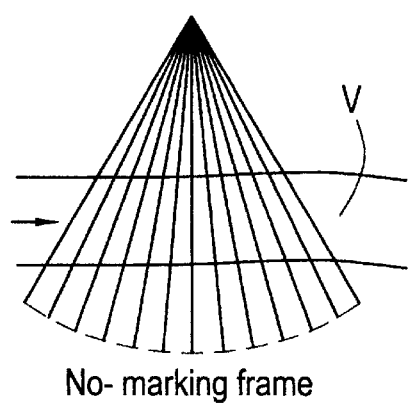

FIG. 4(*a*) is an explanatory diagram of a marking frame produced by the ultrasonic diagnostic apparatus 100.

The marking frame is defined to be an image of a frame which is produced by the transmission of an ultrasonic wave at the strength for the dispersion of contrast agent for part (shown by the bold lines) of a number of sonic beams which form one frame and the transmission of an ultrasonic wave at the strength for no dispersion of contrast agent for other sonic beams (shown by the thin lines), and the formation of an image for one frame from received signals which correspond to the ultrasonic wave transmission.

FIG. 4(*b*) is an explanatory diagram of a no-marking frame produced by the ultrasonic diagnostic apparatus 100.

The no-marking frame is defined to be an image of a frame which is produced by the transmission of an ultrasonic wave at the strength for the dispersion of contrast agent for all of a number of sonic beams which form one frame, and the formation of an image for one frame from received signals which correspond to the ultrasonic wave transmission.

Figure 5:
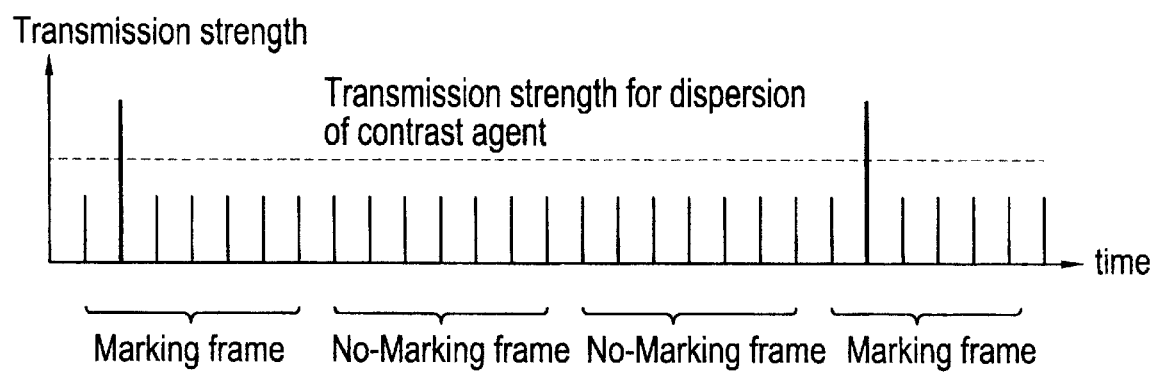
FIG. 5 is an explanatory diagram showing the transmission order for forming frames based on the first embodiment.
Figure 6A:
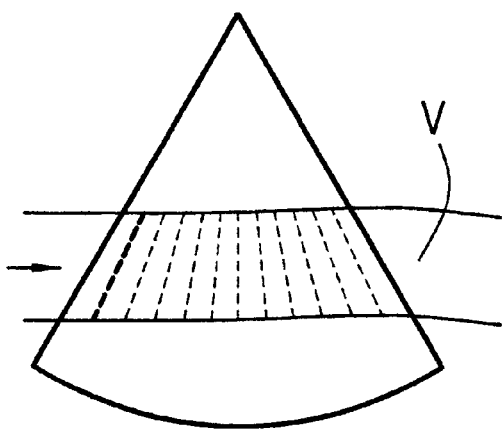
FIG. 6 is a set of diagrams showing examples of ultrasonic images produced by the ultrasonic diagnostic apparatus based on the first embodiment.
Figure 6B:
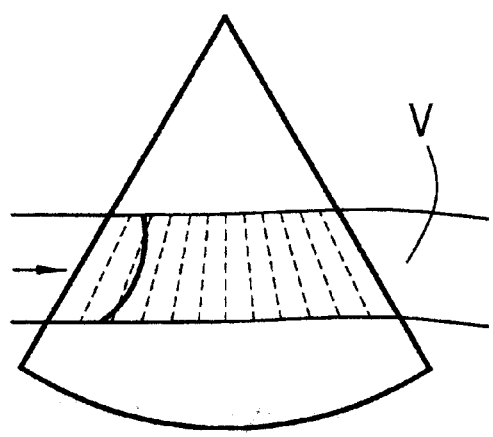
Figure 6C:
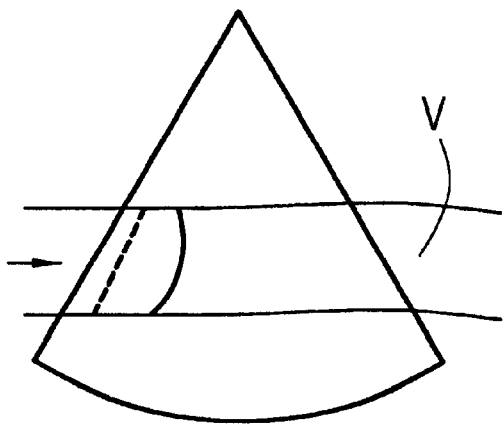
Figure 6D:
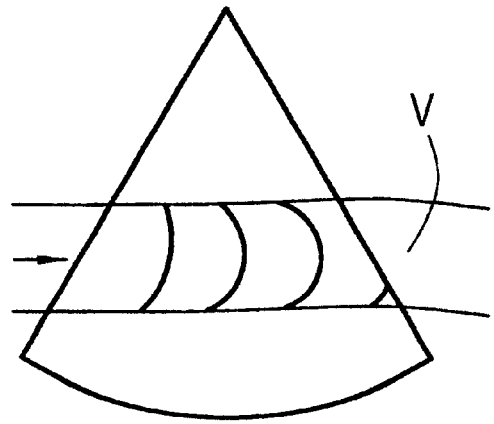

FIG. 5 is an explanatory diagram showing the transmission time points and transmission strengths of sonic beams of the ultrasonic diagnostic apparatus 100.

Vertical line segments aligning along the time axis represent transmission time points and transmission strengths of sonic beams which form the frames.

Following the imaging for a marking frame, imaging for no-marking frames is carried out continuously, and imaging for another marking frame is carried out after such a time length that the flow range is present within the view field, with these operations being repeated.

Providing a time difference, which is based on the heart beat, between the timing of ultrasonic transmission for a marking frame at the strength for the dispersion of contrast agent and the timing of ultrasonic transmission for the next marking frame at the strength for the dispersion of contrast agent enables the proper observation of a pulsing flow. The time difference based on the heart beat may be a multiple of the period of heart beat measured with an electrocardiograph, or may be a multiple of an approximate heart beat period (e.g.,1 second).

FIG. 6 is a set of explanatory diagrams of images produced by the ultrasonic diagnostic apparatus 100.

Shown by (a) is a first marking frame, in which case the contrast agent on the sonic beam (bold dashed line) at the transmission strength for the dispersion of contrast agent disperses, whereas the contrast agent on the sonic beams (thin dashed line) at the transmission strength for no dispersion of contrast agent does not disperse.

Shown by (b) is a no-marking frame which follows the first marking frame, in which case the portion (bold line) where the contrast agent has dispersed in the first marking frame has a weaker echo than other portion and seems to be the black void. Thin dashed lines represent sonic beams at the transmission strength for no dispersion of contrast agent.

Shown by (c) is a second marking frame, in which case only the contrast agent on the sonic beam (bold dashed line) at the transmission strength for the dispersion of contrast agent disperses, as in the case of (a). The portion (bold line) where the contrast agent has dispersed in the first marking frame seems to be the black void.

Shown by (d) is an image after the fifth or later marking frame, in which the portions (bold line) where the contrast agent has dispersed in the preceding marking frames seem to be stripes of the black void.

The ultrasonic diagnostic apparatus 100 of the foregoing first embodiment presents a stripe pattern appended to a flow which intersects the direction of sonic beams as shown by (d) in FIG. 6, whereby it becomes possible to visually recognize the time-wise change at a glance.

Second embodiment:

The arrangement of an ultrasonic diagnostic apparatus based on the second embodiment of this invention is identical to that shown in FIG. 3.

Figure 7A:
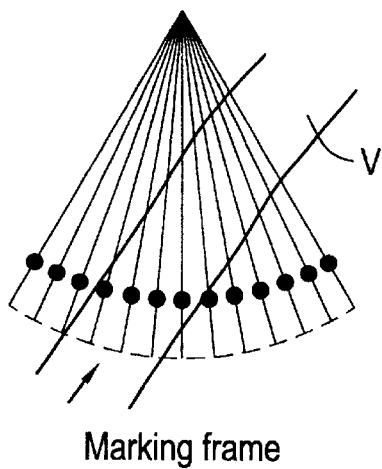
FIG. 7 is an explanatory diagram of a marking frame and no-marking frame based on the second embodiment.
Figure 7B:
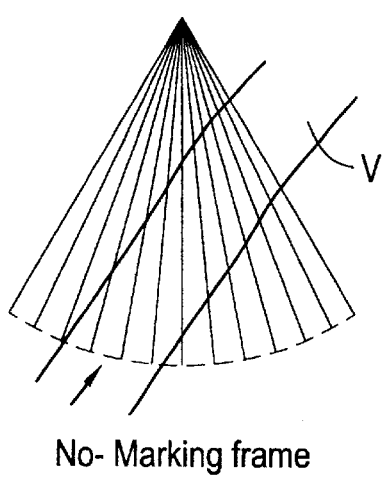

FIG. 7(*a*) is an explanatory diagram of a marking frame produced by the ultrasonic diagnostic apparatus of the second embodiment.

The marking frame is defined to be a frame produced by the concentrated transmission of an ultrasonic wave at the strength for the dispersion of contrast agent for a certain depth (indicated by black dots) of a number of sonic beams (thin lines) which form one frame and the transmission of an ultrasonic wave at the strength for no dispersion of contrast agent for other depths, and the formation of an image for one frame from received signals which correspond to the ultrasonic wave transmission. A certain depth on sonic beams may be replaced with a certain depth seen from the ultrasonic probe.

FIG. 7(*b*) is an explanatory diagram of a no-marking frame.

The no-marking frame is defined to be a frame which is produced by the transmission of an ultrasonic wave at the strength for no dispersion of contrast agent for all of a number of sonic beams which form one frame, and the formation of an image for one frame from received signals which correspond to the ultrasonic wave transmission.

Figure 8:
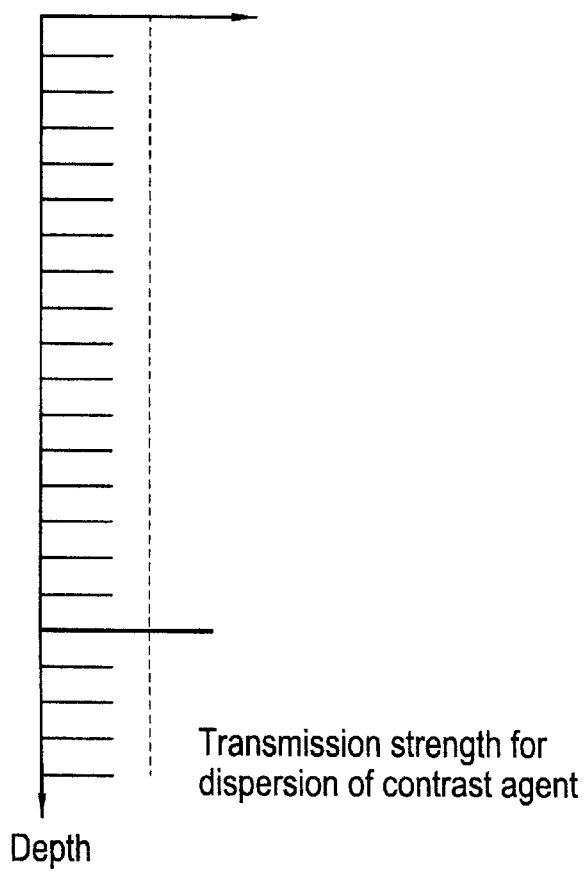
FIG. 8 is an explanatory diagram of the transmission strength for the marking frame based on the second embodiment.
Figure 9A:
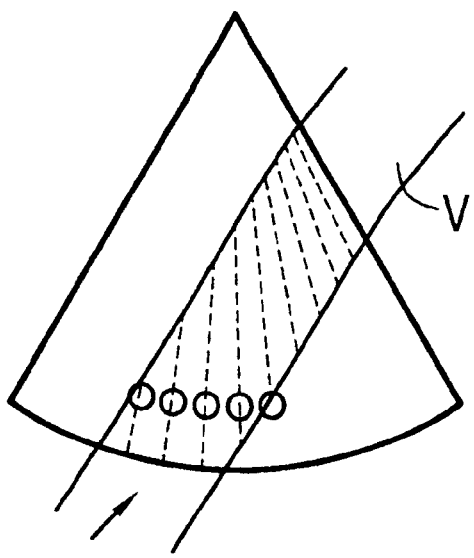
FIG. 9 is a set of diagrams showing examples of ultrasonic images produced by the ultrasonic diagnostic apparatus based on the second embodiment.
Figure 9B:
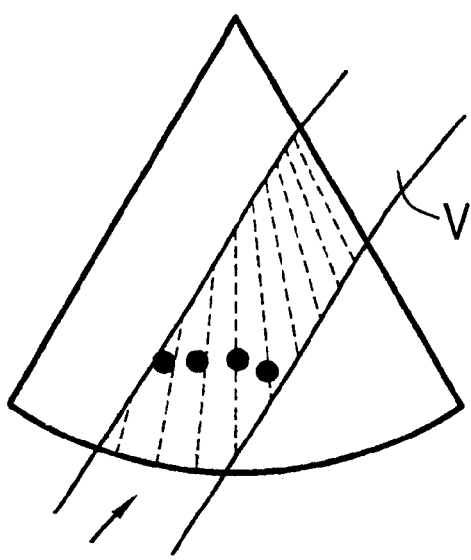
Figure 9C:
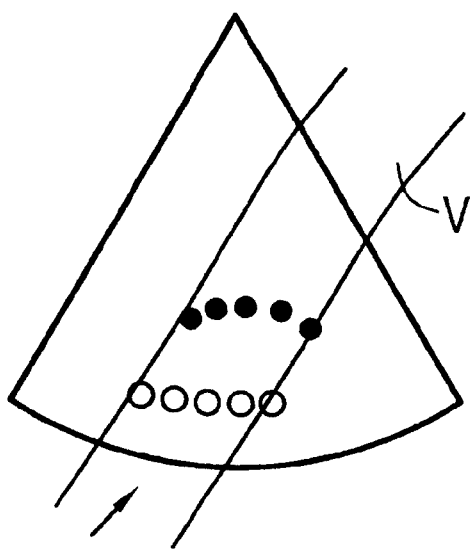
Figure 9D:
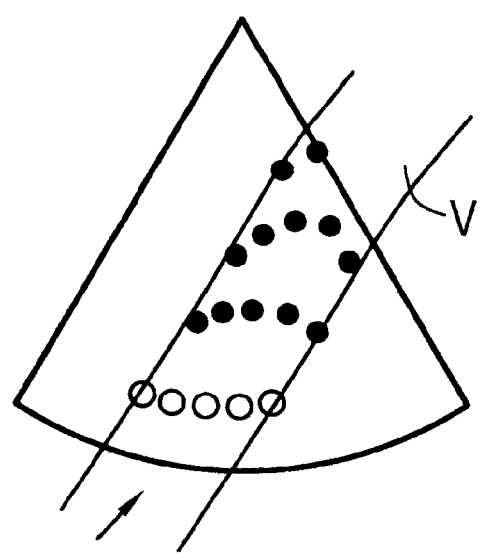

FIG. 8 is an explanatory diagram showing the depths and transmission strengths of sonic beams used for the marking frame.

Lateral line segments aligning on the depth axis represent transmission strengths.

Also in the second embodiment, following the imaging of a marking frame, imaging for no-marking frames is carried out continuously, and imaging for another marking frame is carried out after such a time length that the flow range is present within the view field, with these operations being repeated.

Providing a time difference, which is based on the heart beat, between the timing of ultrasonic transmission for a marking frame at the strength for the dispersion of contrast agent and the timing of ultrasonic transmission for the next marking frame at the strength for the dispersion of contrast agent enables the proper observation of a pulsing flow. The time difference based on the heart beat may be a multiple of the period of heart beat measured with an electrocardiograph, or may be a multiple of an approximate heart beat period (e.g.,1 second).

FIG. 9 is a set of explanatory diagrams of images produced by the ultrasonic diagnostic apparatus of the second embodiment.

Shown by (a) is a first marking frame, in which case the contrast agent in a portion of the depth (white dots) where the contrast agent is to be dispersed disperses, whereas the contrast agent in other portion does not disperse. Thin dashed lines represent sonic beams at the transmission strength for no dispersion of contrast agent.

Shown by (b) is a no-marking frame which follows the first marking frame, in which case the portion (black dots) where the contrast agent has dispersed in the first marking frame has weaker echoes than other portion and seems to be the black void.

Shown by (c) is a second marking frame, in which case only the contrast agent at the depth (white dots) for the dispersion of contrast agent disperses, as in the case of (a). The portion (black dots) where the contrast agent has dispersed in the first marking frame seems to be the black void.

Shown by (d) is an image after the fourth or later marking frame, in which the portions (black dots) where the contrast agent has dispersed in the preceding marking frames seem to be stripes of the black void.

The ultrasonic diagnostic apparatus of the foregoing second embodiment presents a stripe pattern appended to a flow which is virtually parallel to the direction of sonic beams as shown by (d) in FIG. 9, whereby it becomes possible to visually recognize the time-wise change at a glance.

Third embodiment:

The arrangement of an ultrasonic diagnostic apparatus based on the third embodiment of this invention is identical to that shown in FIG. 3.

Figure 10A:
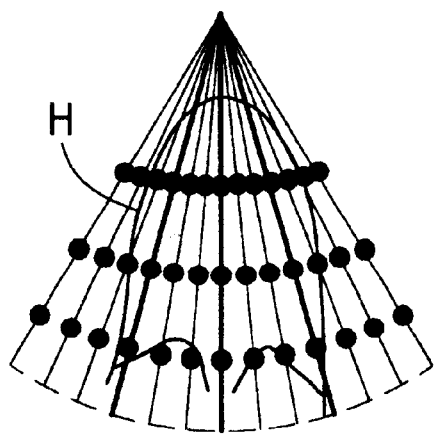
FIG. 10 is an explanatory diagram of a marking frame and no-marking frame based on the third embodiment.

FIG. 10(*a*) is an explanatory diagram of a marking frame produced by the ultrasonic diagnostic apparatus of the third embodiment.

The marking frame is defined to be a frame produced by the transmission of an ultrasonic wave at the strength for the dispersion of contrast agent for two or more spaced-out sonic beams (bold lines) among a number of sonic beams which form one frame and the transmission of an ultrasonic wave for other sonic beams at the strength for the dispersion of contrast agent for two or more spaced-out positions of a certain depth (black dots) and at the strength for no dispersion of contrast agent for other depths, and the formation of an image for one frame from received signals which correspond to the ultrasonic transmission. A certain depth on sonic beams may be replaced with a certain depth seen from the ultrasonic probe.

Figure 10B:
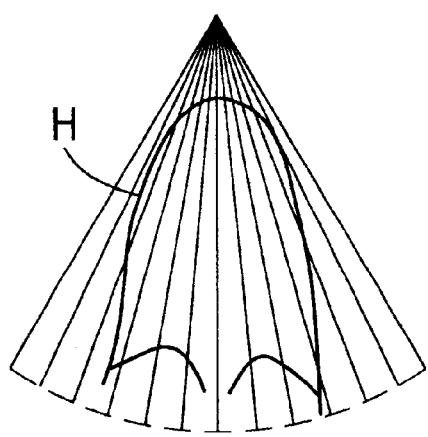

FIG. 10(b) is an explanatory diagram of a no-marking frame.

The no-marking frame is defined to be a frame which is produced by the transmission of an ultrasonic wave at the strength for no dispersion of contrast agent for all of a number of sonic beams which form one frame, and the formation of an image for one frame from received signals which correspond to the ultrasonic wave transmission.

Also in the third embodiment, following the imaging of a marking frame, imaging for no-marking frames is carried out continuously, and imaging for another marking frame is carried out after such a time length that the flow range is present within the view field, with these operations being repeated.

Providing a time difference, which is based on the heart beat, between the timing of ultrasonic transmission for a marking frame at the strength for the dispersion of contrast agent and the timing of ultrasonic transmission for the next marking frame at the strength for the dispersion of contrast agent enables the proper observation of a pulsing flow. The time difference based on the heart beat may be a multiple of the period of heart beat measured with an electrocardiograph, or may be a multiple of an approximate heart beat period (e.g.,1 second).

Figure 11:
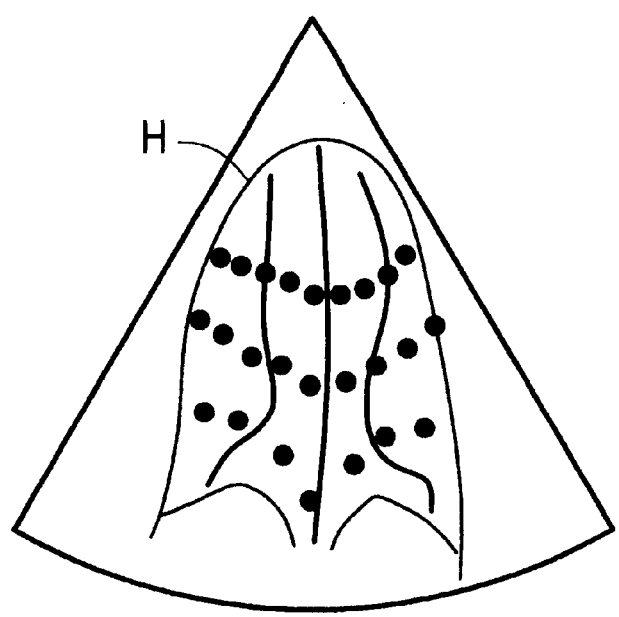
FIG. 11 is a diagram of an ultrasonic image produced by the ultrasonic diagnostic apparatus based on the third embodiment.

FIG. 11 is an explanatory diagram of an image produced by the ultrasonic diagnostic apparatus of the third embodiment.

The portions of marking frames where the contrast agent has dispersed (bold lines and black dots) seem to be a lattice of the black void.

The ultrasonic diagnostic apparatus based on the third embodiment presents stripe patterns in both the direction orthogonal to the direction of sonic beams and the direction of flow which is virtually parallel to the direction of sonic beams (i.e., in a shape of lattice) as shown in FIG. 11, whereby it becomes possible to visually recognize at a glance the time-wise change of particularly a two-dimensional flow in the cardiac ventricle and atrium.

Many widely different embodiments of the invention may be configured without departing from the spirit and the scope of the present invention. It should be understood that the present invention is not limited to the specific embodiments described in the specification, except as defined in the appended claims.

What is claimed is:

1. A method of ultrasonic imaging comprising the steps of:
   transmitting an ultrasonic wave of a particular strength sufficient to disperse a contrast agent for only a part of and less than the total number of a first set of sonic beams forming a first frame;
   transmitting a plurality of ultrasonic waves of a strength which does not disperse the contrast agent for all of the total number of a second set of sonic beams forming a second frame; and
   producing an image for a third frame from received signals which correspond to said ultrasonic waves.

2. A method of ultrasonic imaging comprising the steps of:
   transmitting one or more ultrasonic waves of a particular strength to disperse a contrast agent at a particular depth or band of depths of a total number of sonic beams forming a first frame;
   transmitting a plurality of ultrasonic waves of a strength which does not disperse the contrast agent for all of the total number of a second set of sonic beams forming a second frame; and
   producing an image for a third frame from received signals which correspond to said ultrasonic waves.

3. The method of claim 1, further comprising the steps of transmitting one or more ultrasonic waves of a particular strength to disperse said contrast agent at a particular depth or band of depths of a total number of sonic beams forming a frame which is combined with said first frame.

4. The method of claim 1, 2, or 3, further comprising the step of transmitting a second ultrasonic wave of a particular strength sufficient to disperse the contrast agent in the same frame as said first frame.

5. The method of claim 1, 2, or 3, further comprising the steps of:
   transmitting a plurality of ultrasonic waves of a strength which does not disperse the contrast agent for all of the total number of second set of sonic beams forming the second frame;
   producing an image for a fourth frame from signals received corresponding to the ultrasonic waves; and
   interposing said fourth frame between said first and said second frames.

6. The method of claim 1, 2 or 3, further comprising the steps of:
   transmitting another ultrasonic wave of a particular strength sufficient to disperse said contrast agent for a part of and less than the total number of a third set of sonic beams forming a third frame; and
   wherein timing of the ultrasonic waves of the first frame and the third frame are based on timing of a heart beat.

7. The method of claim 1, 2 or 3, wherein two ultrasonic waves of a particular strength sufficient to disperse the contrast agent are provided for only a part of and less than the total number of first set of sonic beams forming the first frame.

8. An ultrasonic diagnostic apparatus comprising:
   an ultrasonic probe;
   transmission and reception means for transmitting an ultrasonic wave from said ultrasonic probe and for receiving a signal which corresponds to the ultrasonic wave transmitted thereby;
   means for controlling said transmission means so as to cause
      transmitting an ultrasonic wave of a particular strength sufficient to disperse a contrast agent for only a part of and less than the total number of a first set of sonic beams forming a first frame; and
      transmitting a plurality of ultrasonic waves of a strength which does not disperse the contrast agent for all of the total number of a second set of sonic beams forming a second frame; and
   imaging means for producing an image for a third frame from the received signals.

9. An ultrasonic diagnostic apparatus comprising:

an ultrasonic probe;

transmission and reception means for transmitting and ultrasonic wave from said ultrasonic probe and for receiving a signal which corresponds to the ultrasonic wave transmitted thereby;

means for controlling said transmission means so as to cause transmitting one or more ultrasonic waves of a particular strength to disperse a contrast agent at a particular depth or band of depths of a total number of sonic beams forming a first frame;

transmitting a plurality of ultrasonic waves of a strength which does not disperse the contrast agent for all of the total number of a second set of sonic beams forming a second frame; and imaging means for producing an image for a third frame from the received signals.

10. The apparatus of claim 8, wherein said means for controlling comprises means for causing said transmission means to transmit one or more ultrasonic waves of a particular strength to disperse said contrast agent at a particular depth or band of depths of a total number of sonic beams forming a frame which is combined with said first frame.

11. The apparatus of claim 8, 9 or 10, wherein said means for controlling comprises means for causing said transmission means to transmit a second ultrasonic wave of a particular strength sufficient to disperse the contrast agent in the same frame as said first frame.

12. the apparatus of claim 8, 9 or 10, wherein said means for controlling comprises means for causing said transmission means to transmit a plurality of ultrasonic waves of a strength which does not disperse the contrast agent for all of the total number of second set of sonic beams forming the second frame;

produce an image for a fourth frame from signals received corresponding to the ultrasonic waves; and interposing said fourth frame between said first frame and said second frame.

13. The apparatus of claim 8, 9 or 10, wherein said means for controlling comprises means for causing said transmission means to transmit another ultrasonic wave of a particular strength sufficient to disperse said contrast agent for a part of and less than the total number of a third set of sonic beams forming a third frame; and wherein timing of the ultrasonic waves of the first frame and the third frame are based on time of a heart beat.

14. The apparatus of claim 8, 9 or 10, wherein said means for controlling comprises means for causing said transmission means to transmit two ultrasonic waves of a particular strength sufficient to disperse said contrast agent for only a part of and less than the total number of first set of sonic beams forming the first frame.

* * * * *